(12) United States Patent
Blankenship et al.

(10) Patent No.: US 10,478,548 B2
(45) Date of Patent: Nov. 19, 2019

(54) HOSPITAL SUPPORT POLES WITH ONBOARD POWER UNITS

(71) Applicant: Skytron, LLC, Grand Rapids, MI (US)

(72) Inventors: Samuel A. Blankenship, Anoka, MN (US); Peter B. Blankenship, Anoka, MN (US); Richard Baumhardt, Breckenridge, MN (US)

(73) Assignee: Skytron, LLC, Grand Rapids, MI (US)

( * ) Notice: Subject to any disclaimer, the term of this patent is extended or adjusted under 35 U.S.C. 154(b) by 103 days.

(21) Appl. No.: 15/566,946

(22) PCT Filed: Mar. 18, 2016

(86) PCT No.: PCT/US2016/023075
§ 371 (c)(1),
(2) Date: Oct. 16, 2017

(87) PCT Pub. No.: WO2016/167917
PCT Pub. Date: Oct. 20, 2016

(65) Prior Publication Data
US 2018/0133393 A1    May 17, 2018

Related U.S. Application Data

(60) Provisional application No. 62/221,409, filed on Sep. 21, 2015, provisional application No. 62/207,106, (Continued)

(51) Int. Cl.
*F16M 11/42* (2006.01)
*A61M 5/14* (2006.01)
*A61G 12/00* (2006.01)

(52) U.S. Cl.
CPC ......... *A61M 5/1415* (2013.01); *A61G 12/007* (2013.01); *A61M 2209/084* (2013.01); *F16M 11/42* (2013.01)

(58) Field of Classification Search
USPC ....................................... 248/125.8
See application file for complete search history.

(56) References Cited

U.S. PATENT DOCUMENTS

D122,497 S  *  9/1940  McCarthy .................... 439/721
4,384,688 A     5/1983  Smith
(Continued)

FOREIGN PATENT DOCUMENTS

EP    1985275 A2    10/2008

OTHER PUBLICATIONS

"Deluxe Pole Mounted Hospital Grade Power Strip", WT Farley Inc., available at http://www.wtfarley.com/Deluxe-Pole-Mounted-Hospital-Grade-Power-strip-_p_541 and available at least as of Jun. 17, 2015.
(Continued)

*Primary Examiner* — Monica E Millner
(74) *Attorney, Agent, or Firm* — Warner Norcross + Judd LLP

(57) ABSTRACT

Embodiments of the invention relate to poles with wheels with an onboard power unit that be longitudinally fixed in place and positioned about a medial position of the pole or may be configured to rise and lower in concert with wheels supporting the floor when on the floor and that can hold medical and/or accessory equipment, typically in a clinical or hospital environment.

19 Claims, 13 Drawing Sheets

Related U.S. Application Data filed on Aug. 19, 2015, provisional application No. 62/148,398, filed on Apr. 16, 2015.

(56) References Cited

U.S. PATENT DOCUMENTS

| | | | | |
|---|---|---|---|---|
| 4,520,239 | A | 5/1985 | Schwartz | |
| D325,723 | S * | 4/1992 | Gary | D13/139.4 |
| 6,302,743 | B1 | 10/2001 | Chiu et al. | |
| 6,969,031 | B2 | 11/2005 | Ugent et al. | |
| 7,264,514 | B2 | 9/2007 | Hsu et al. | |
| 7,626,119 | B2 | 12/2009 | Axland et al. | |
| 7,753,682 | B2 | 7/2010 | Gerard | |
| 7,777,995 | B2 * | 8/2010 | Malkus | H01R 25/003 |
| | | | | 361/42 |
| 7,874,410 | B2 * | 1/2011 | Fulbrook | A61M 5/1415 |
| | | | | 191/12 R |
| 8,292,656 | B2 * | 10/2012 | Mydlarz | H01R 13/60 |
| | | | | 439/501 |
| 9,543,692 | B2 * | 1/2017 | Shomali | H01R 13/5224 |
| 10,112,004 | B2 * | 10/2018 | Brown | A61M 5/1418 |
| 2005/0116126 | A1 * | 6/2005 | Ugent | A61M 5/1415 |
| | | | | 248/129 |
| 2007/0159772 | A1 | 7/2007 | Morice | |
| 2008/0116157 | A1 | 5/2008 | Fulbrook et al. | |
| 2009/0046402 | A1 | 2/2009 | Malkus et al. | |
| 2009/0085317 | A1 * | 4/2009 | Livengood | A61H 3/04 |
| | | | | 280/79.3 |
| 2009/0142172 | A1 | 6/2009 | Blankenship et al. | |
| 2010/0081318 | A1 | 4/2010 | Mydlarz | |
| 2013/0181100 | A1 * | 7/2013 | Blankenship | A61M 5/1415 |
| | | | | 248/129 |
| 2015/0118896 | A1 | 4/2015 | Shomali | |
| 2015/0335774 | A1 | 11/2015 | Gomez | |
| 2016/0022900 | A1 | 1/2016 | Pryor et al. | |

OTHER PUBLICATIONS

"Pole Mounted Hospital Grade Power strip", WT Farley Inc., available at http://www.wtfarley.com/Pole-Mounted-Hospital-Grade-Power-strip_p_525 and available at least as of Jun. 17, 2015.

"Medical Grade Power Strips", Product Bulletin, Leviton Manufacturing Co. Inc., 2014.

Martin, Melissa, "Sail Through Your Next Hospital Inspection with Medical Grade Power Strips from Leviton", published on the Leviton Blog website at blog.leviton.com, Dated Dec. 23, 2013.

"Pedigo Infusion Pump Outlet Strip", Universal Medical, available at http://www.universalmedicalinc.com/pedigo-infusion-pump-outlet-strip and available at least as of Jun. 17, 2015.

"For Patient-Care Vicinity—UL1363A Medical-Grade Power Strip with 4 Hospital-Grade Outlets, 10 ft. Cord, Drip Shield, Cord Wrap", Tripp Lite, available at http://www.tripplite.com/medical-grade-power-strip-4-outlets-10-ft-cord-integrated-cord-wrap-patient-care-areas-PS410HGOEMX and available at least as of Jun. 17, 2015.

Medreel advertisement, APC Group Inc., 2015.

PCT International Search Report completed on May 31, 2016 for Application No. PCT/US2016/023075, filed on Mar. 18, 2016.

PCT International Written Opinion for Application No. PCT/US2016/023075, filed on Mar. 18, 2016.

* cited by examiner

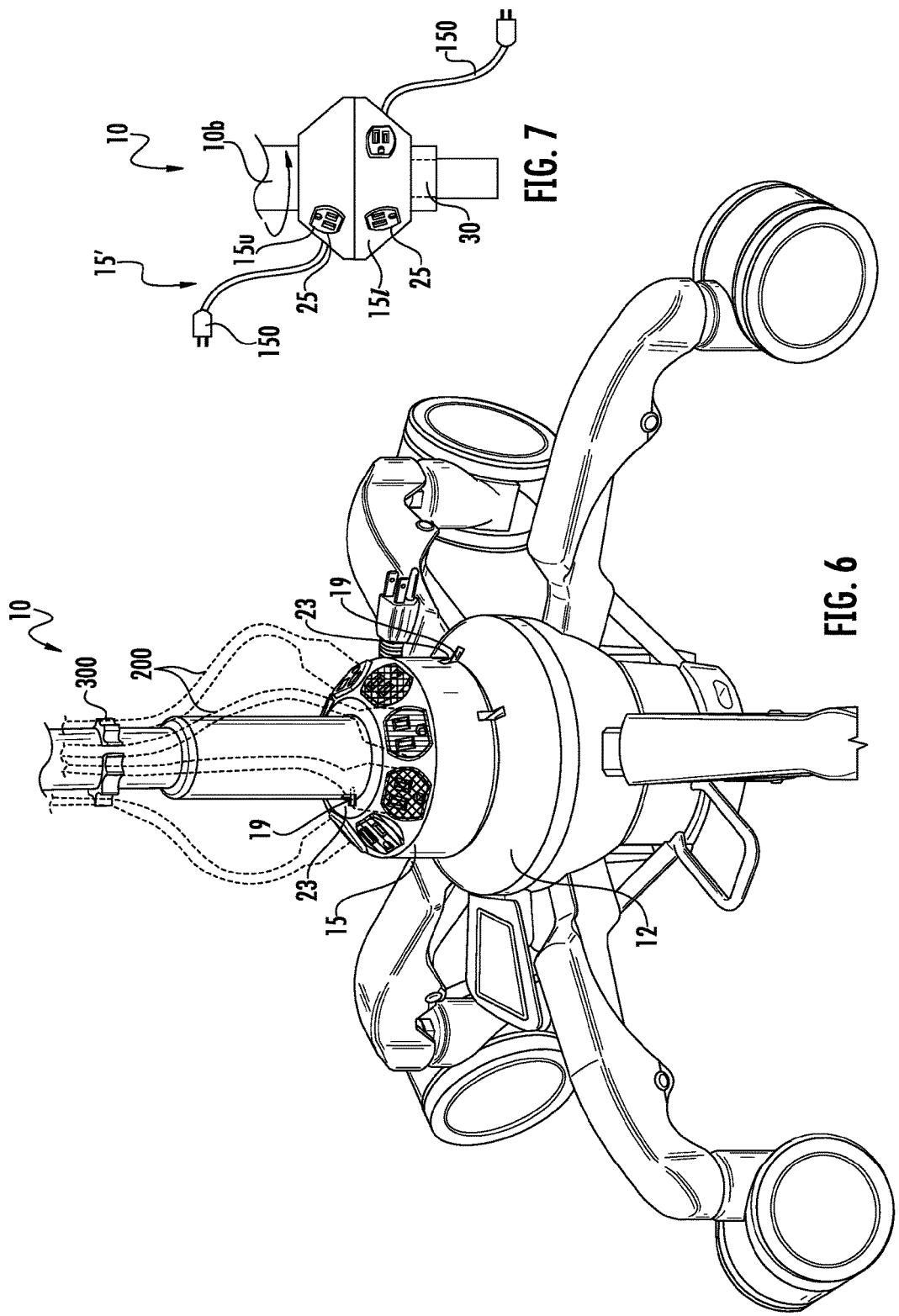

HOSPITAL SUPPORT POLES WITH ONBOARD POWER UNITS

RELATED APPLICATIONS

This application claims the benefit of and priority to U.S. Provisional Application Ser. No. 62/148,398 filed Apr. 16, 2015, U.S. Provisional Application Ser. No. 62/207,106 filed Aug. 19, 2015, and U.S. Provisional Application Ser. No. 62/221,409 filed Sep. 21, 2015 the contents of which are hereby incorporated by reference as if recited in full herein.

FIELD OF THE INVENTION

The invention relates to hospital accessory poles such as IV poles.

BACKGROUND

For many years, patients needing intravenous (IV) fluid transfusions have been moved by a patient transportation apparatus such as a wheelchair, wheeled bed, stretcher, gurney or the like while receiving intravenous (IV) transfusions by the use of mobile IV poles. These IV poles, however, suffer from a number of drawbacks.

SUMMARY

Embodiments of the invention relate to poles for hospital accessories that include an onboard power unit. The poles are typically for a clinical or hospital environment, and can dock to various devices such as booms, beds, wheelchairs, walkers, wagons, and the like.

The poles can have a plurality of legs which hold wheels, typically casters.

The poles can have wheels that can be small wheels, larger wheels combinations of smaller and larger wheels, with or without casters.

In some embodiments, the legs are not retractable but the mast may be extendable/retractable.

In some embodiments, the legs can be moved between an extended configuration where the wheels contact a floor and a retracted configuration where the legs are drawn inward and the wheels are lifted to reside off the floor.

A medical accessory support pole, comprising: an elongate pole body; a plurality of wheels attached to the pole body; and an onboard power unit held by the pole body, comprising: a housing having a downwardly extending cylindrical channel surrounding a segment of the pole body; a plurality of circumferentially spaced apart electrical receptacles; and a power cord in electrical communication with the electrical receptacles extending outward from the housing.

The pole can include a power cord retraction mechanism held by the housing in communication with the power cord to allow automatic or semi-automatic retraction of the power cord into the housing.

The power cord can have a length of between 5-12 feet, and, in a fully or partially retracted configuration, a length of the power cord can reside inside the housing in stacked circular layers about the cylindrical channel.

The retraction mechanism can include a rotation coupler that can be in communication with a compartment holding a length of the power cord.

The housing can have a neck that angles out to a receptacle surface, then extends a vertical distance to define a cord compartment.

The cord compartment can be rotatable inside the housing about a pole axis of a centerline of the cylindrical channel.

The pole can be a transformable pole having a plurality outwardly extending legs holding a respective wheel. The transformable pole can have a first extended configuration with the legs extending outward away from the pole body with the wheels on a floor and a second configuration with the legs are retracted to reside closer to the pole body and the wheels are lifted off the floor. The onboard power unit can be configured to longitudinally slide up and down in concert with a base as the legs retract and extend, respectively.

The pole can include at least one cord grip attached to the pole body. The cord grip can include a plurality of circumferentially spaced apart and longitudinally extending accessory cord channels for holding segments of longitudinally extending accessory power cords.

At least one of the electrical receptacles can have an externally visual color that is different from one or more other of the electrical receptacles.

The power unit housing can be rotatable about a vertical pole axis of the pole body.

One or more of the electrical receptacles can have a different socket orientation from another of the electrical receptacles.

One or more of the electrical receptacles can be rotated to provide a desired socket orientation.

The housing can have an angled outer surface that extends away from the cylindrical channel and merges into a vertical outer wall. The angled outer surface can be angled at between 30-60 degrees from horizontal.

The pole can include wings held by an upper portion of the pole body and a base held adjacent the wheels. The housing can reside a distance above the wheels by between 3-6 feet to reside closer to the wings of the pole than the base.

The pole body can include a docking alignment key member circumferentially extending between 15-45 degrees and longitudinally extending between 1-5 inches of a segment of the pole body. The segment of the pole body with the key member can have a diameter that is less than a diameter of at least an adjacent lower portion of the pole body. The housing can reside a distance above the wheels by between 3-6 feet to reside above the key member. The housing can have an outer wall that extends radially outward a greater distance from the pole body than the key member.

Other embodiments are directed to a medical accessory support pole that includes: an elongate pole body; a base attached to a lower portion of the pole body comprising a plurality outwardly extending legs; and a plurality of wheels attached to the legs. The legs have a first extended configuration with the legs extending outward away from the pole body with the wheels on a floor and a second configuration where the legs are retracted to reside closer to the pole body and the wheels are lifted off the floor. The pole also includes an onboard power unit attached to the pole body. The onboard power unit includes: a housing having a downwardly extending cylindrical channel surrounding a segment of the pole; a plurality of circumferentially spaced apart electrical receptacles; a power cord in electrical communication with the electrical receptacles extending outward from the housing; and a power cord retraction mechanism held by the housing in communication with the power cord to allow automatic or semi-automatic retraction of the power cord into the housing. The power cord can have a length of between about 5 feet and about 12 feet, and, in a fully or partially retracted configuration, a length of the power cord resides inside the housing in stacked circular layers about the cylindrical channel. The onboard power unit is configured to longitudinally slide up and down in concert with the base as the legs retract and extend, respectively.

The housing can be rotatable about the pole body. The housing can include a power cord compartment that is configured to rotate inside the housing about the pole.

Still other embodiments are directed to a medical accessory support pole that includes: an elongate pole body; a base attached to a lower portion of the pole body comprising a plurality outwardly extending legs; and a plurality of wheels attached to the legs. The legs have a first extended configuration with the legs extending outward away from the pole body with the wheels on a floor and a second configuration where the legs are retracted to reside closer to the pole body and the wheels are lifted off the floor. The pole also has an onboard power unit attached to the pole body that includes: a housing having a downwardly extending cylindrical channel surrounding a segment of the pole; a plurality of circumferentially spaced apart electrical receptacles; a power cord in electrical communication with the electrical receptacles extending outward from the housing; and a power cord retraction mechanism held by the housing in communication with the power cord to allow automatic or semi-automatic retraction of the power cord into the housing. The power cord has a length of between about 5 feet and about 12 feet, and, in a fully or partially retracted configuration, a length of the power cord resides inside the housing in stacked circular layers about the cylindrical channel. The pole includes wings held by an upper portion of the pole body. The housing resides a distance above the wheels by between 3-6 feet to reside closer to the wings of the pole than the base.

The pole body can have a docking alignment key member circumferentially extending between 15-45 degrees and longitudinally extending between 1-5 inches about a segment of the pole body. The segment of the pole body with the key member can have a diameter that is less than a diameter of at least an adjacent lower portion of the pole body. The power unit housing can reside above the key member. The housing can include an outer wall that extends radially outward a greater distance from the pole body than the key member.

The housing can be rotatable about the pole body. The housing can include a power cord compartment that is configured to rotate inside the housing about the pole.

Other embodiments are directed to methods of providing power to hospital equipment. The methods include: (i) providing a hospital support pole with a plurality of rollers and/or casters and comprising an on-board power shroud with a plurality of electrical receptacles; (ii) rolling the hospital support pole across a floor; extending a power cord held in a cord compartment of the on-board power shroud to have an exposed length; and (iii) plugging in the power cord to an electrical receptacle of a hospital electrical circuit to power the receptacles of the on-board power shroud.

Optionally, in response to a user unplugging the power cord, automatically retracting the exposed length of the power cord back into the cord compartment.

Optionally, electromechanically or mechanically automatically raising the hospital support pole so that the rollers and/or casters are off floor before, during or after plugging in the power cord.

It is noted that any one or more aspects or features described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner.

These and other aspects of the invention are described in more detail in the accompanying description and drawings.

BRIEF DESCRIPTION OF THE DRAWINGS

FIG. 6 is a side perspective view of an embodiment of the pole with the on-board power unit according to embodiments of the present invention.

FIG. 7 is a schematic illustration of an onboard power unit with stacked electrical receptacles according to embodiments of the present invention.

DETAILED DESCRIPTION

Figure 1:
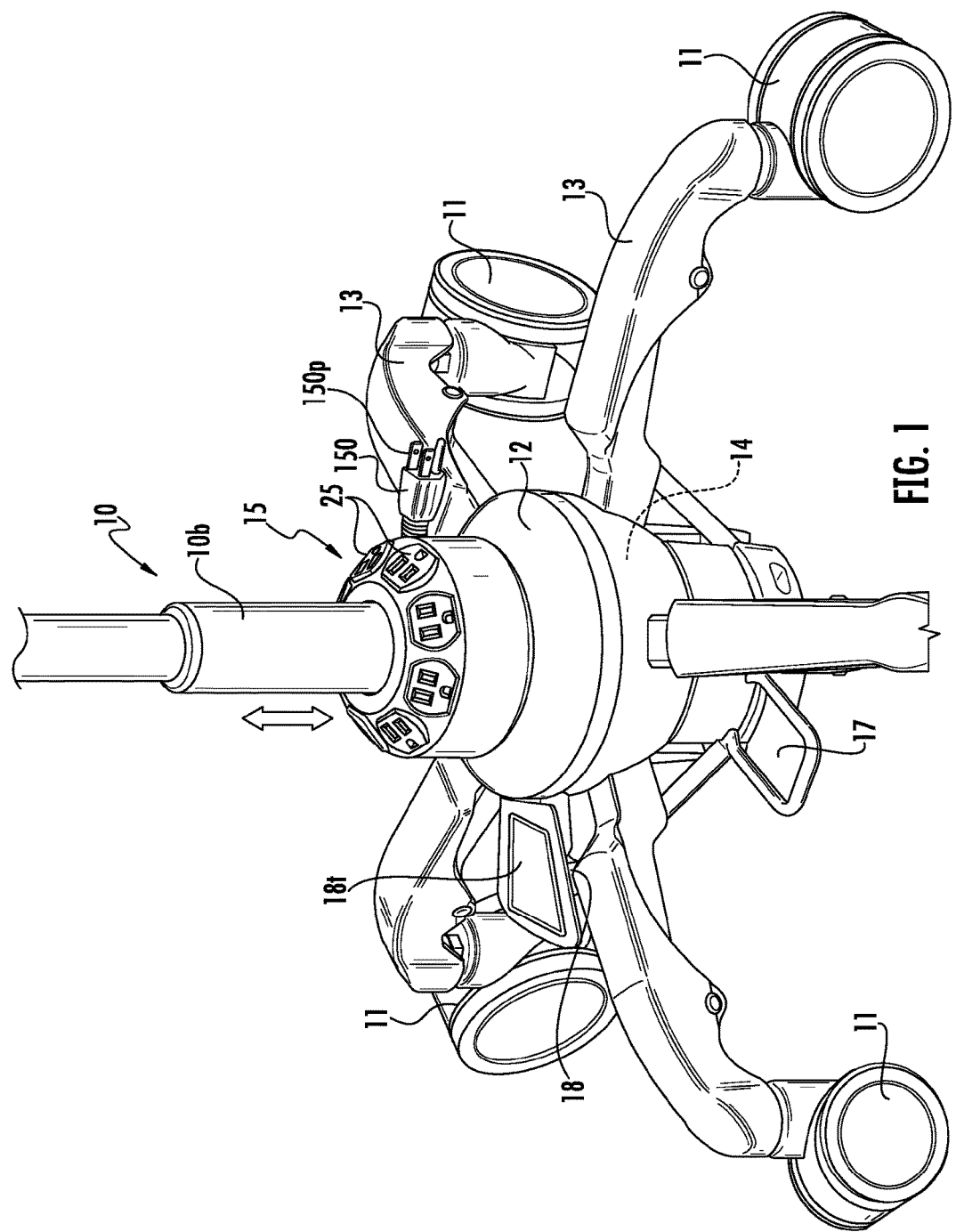
FIG. 1 is a perspective view of a portion of a transformable pole according to embodiments of the present invention.

The present invention now will be described more fully hereinafter with reference to the accompanying drawings, in which illustrative embodiments of the invention are shown. Like numbers refer to like elements and different embodiments of like elements can be designated using a different number of superscript indicator apostrophes (e.g., 90, 90', 90", 90''').

In the drawings, the relative sizes of regions or features may be exaggerated for clarity. This invention may, however, be embodied in many different forms and should not be construed as limited to the embodiments set forth herein; rather, these embodiments are provided so that this disclosure will be thorough and complete, and will fully convey the scope of the invention to those skilled in the art. The term "Fig." (whether in all capital letters or not) is used interchangeably with the word "Figure" as an abbreviation thereof in the specification and drawings. In the figures, certain layers, components or features may be exaggerated for clarity, and broken lines illustrate optional features or operations unless specified otherwise. In addition, the sequence of operations (or steps) is not limited to the order presented in the claims unless specifically indicated otherwise.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath", "below", "bottom", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass orientations of above, below and behind. The device may be otherwise oriented (rotated 90° or at other orientations) and the spatially relative descriptors used herein interpreted accordingly.

The term "about" refers to numbers in a range of +/−20% of the noted value.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. As used herein, the term "and/or" includes any and all combinations of one or more of the associated listed items.

The terms "accessory" and "accessory devices" are used interchangeably to refer to any clinical or hospital device that may be desirable to be provided for and/or moved with a patient using a support pole on wheels such as an IV pole, and can include one or more of IV systems, IV bags, IV bag supports, pumps, pump supports, monitors, monitor supports, tables, trays, oxygen tank/canisters and canister holders 250 (FIG. 3) and the like.

Turning now to the figures, FIG. 1 illustrates a pole 10 with an onboard power unit 15 with a plurality of circumferentially spaced apart plug-in electrical receptacles 25 and a power cord 150. The pole 10 can be a transformable pole. The power cord 150 can have an external male plug-in connector 150p.

Figure 2A:
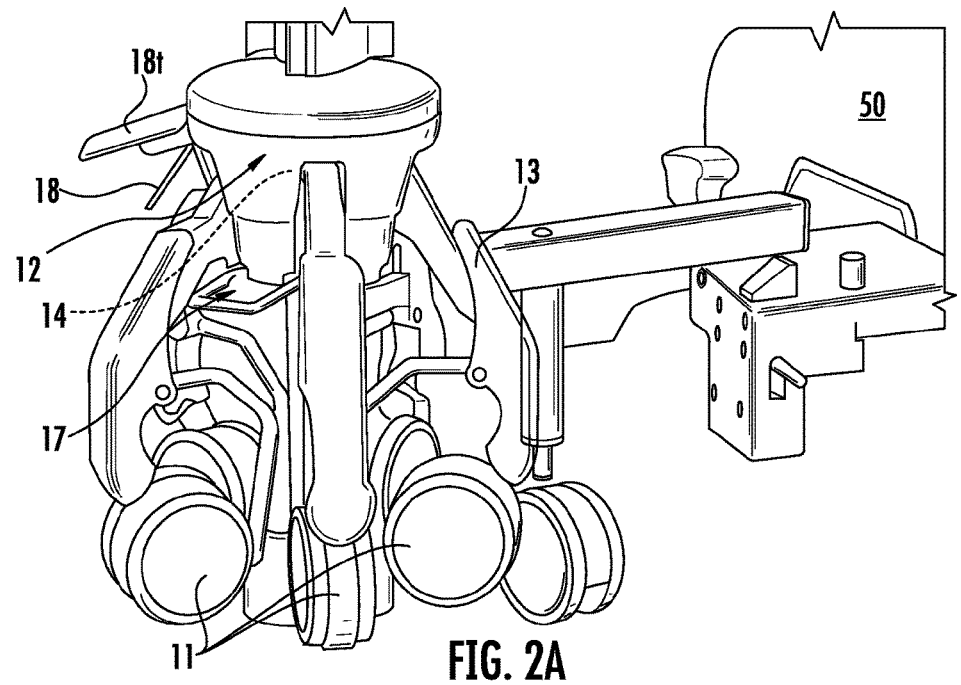
FIGS. 2A and 2B are enlarged views of retracted/stowed configuration and an extended operational configuration, respectively, of a transformable pole according to embodiments of the present invention.
Figure 2B:
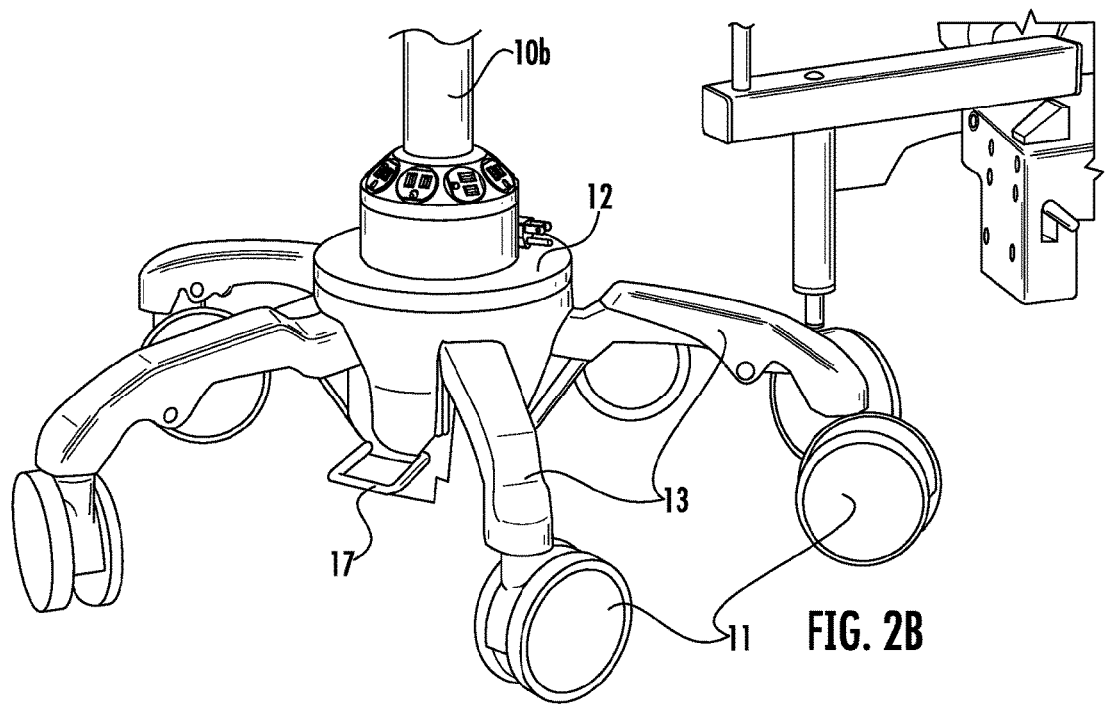

The term "transformable" when referring to some embodiments of the pole 10 means that the pole 10 can transform between at least two different configurations, typically including a stowed configuration with the wheels 11 off of/above a support floor as shown in FIG. 2A and an extended configuration with the wheels 11 on the floor as shown in FIG. 2B with the wheels 11 able to provide a weight bearing support for the upwardly extending tubular pole body 10b. The pole 10 can include a lift mechanism 14 held by the base 12. The lift mechanism 14 can slide up and down relative to a lower end portion of the pole body 10b. The lift mechanism 14 holds legs 13 that are attached to the wheels 11. The legs 13 can pivot inward and outward relative to the base 12 to be able to retract and extend the wheels 11 in the stowed and extended positions, respectively. The pole 10 can include at least one foot lever for moving between the stowed and extended positions.

As shown in FIG. 1, the pole 10 can have a manually-actuated foot lever 18 accessible under a lift tab 18t in communication with the lift mechanism 14 for engaging an onboard (e.g., gas spring) actuator that raises the wheels 11. The pole 10 may also have a second lever 17 for lowering the wheels 11. The second lever 17 can manually lower the wheels 13 from force applied to the second lever 17. In some embodiments, the wheels 11 are caster-type wheels capable of freely rotating along a leg-wheel connection. Although in this particular depiction there are five legs 13 with five four-inch caster-type wheels 11, embodiments with different numbers of legs (such as 1, 2, 3 or 6 or more) and different sized or types of wheels, or combinations of different types or sizes, larger or smaller or combinations of different size wheels may be used.

The lift mechanism 14 may include a gas spring as described in U.S. Pat. No. 7,918,422, the contents of which are hereby incorporated by reference as if recited in full herein. Alternatively, other lift mechanisms 14 including, for example, electric motor or pneumatic driven gears and/or links may be used.

FIGS. 2A and 2B are enlarged views of retracted/stowed configuration and an extended operational configuration, respectively, of a transformable pole 10 that can include the onboard power unit 15 according to embodiments of the present invention.

Figure 3:
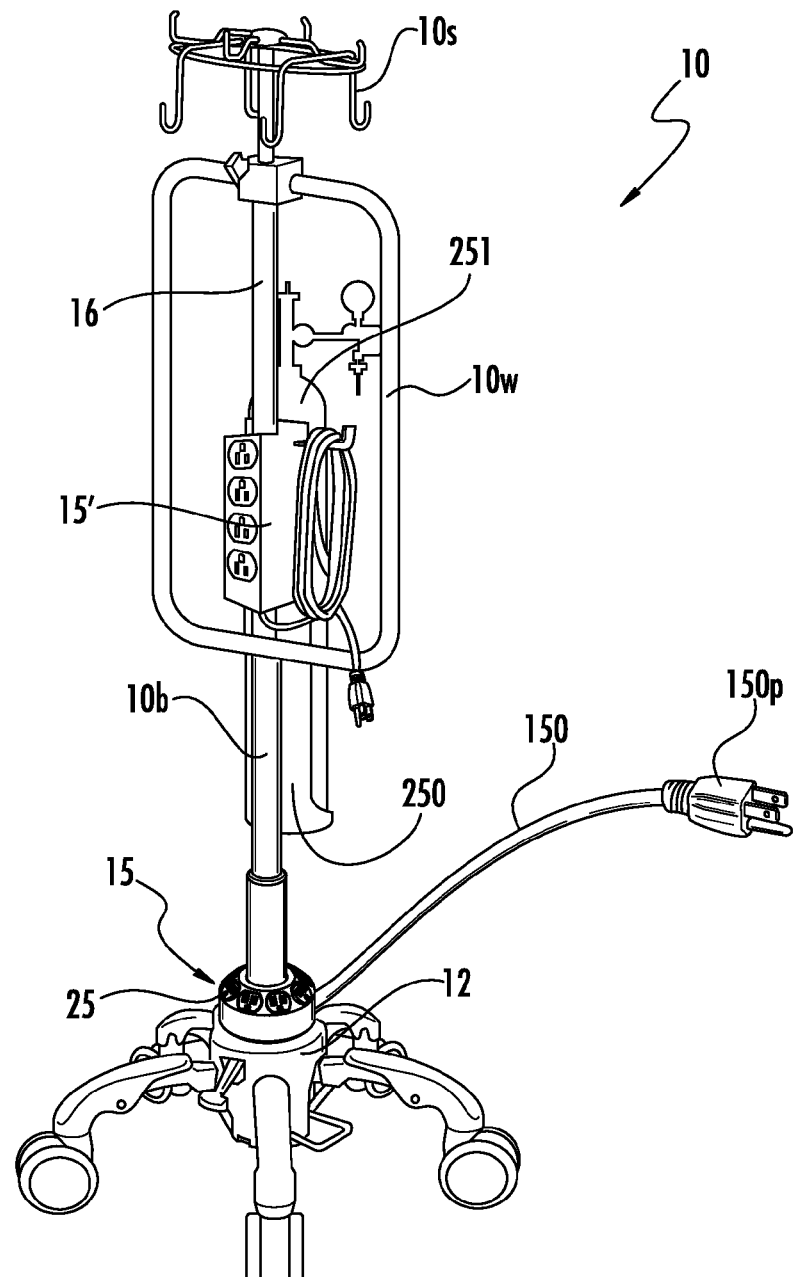
FIG. 3 is a side perspective view of an IV pole that can comprise a power strip unit and/or an oxygen tank holder according to embodiments of the present invention according to embodiments of the present invention.

As shown in FIG. 3, the tubular pole body 10b can include an upper mast 16 residing between wings 10w under a suspension support 10s for suspending bags of fluids for patient administration, such as IV fluids and the like. The wings 10w can support patient monitors and/or other devices. See, e.g., U.S. Pat. Nos. 7,497,407; 7,918,422; 7,735,789; and US Patent Application Publication 2013/0181100, the contents of which are hereby incorporated by reference as if recited in full herein.

As shown in FIG. 3, the pole 10 can include the power unit 15 with the circumferentially spaced apart receptacles 25 and may include a secondary onboard power strip unit 15' and/or a gas canister holder 250 that can releasably hold a gas canister 251.

Turning again to FIG. 1, in some embodiments, the onboard power unit 15 can be configured to longitudinally slide up and down as indicated by the vertically oriented arrow. The power unit 15 can be incorporated into the base 12 or reside above the base 12 and slidably cooperate with the base 12 to be able to slide up and down in concert with the base 12 as the legs 13 retract and extend, respectively. The longitudinal travel can be between 2-10 inches, typically about 4-7 inches, such as about 4 inches, about 5 inches, about 6 inches about or about 7 inches and in particular embodiments can be about 6 inches.

The power cord 150 is preferably configured as a retractable power cord as shown in FIGS. 1 and 4A-4D. However, the power cord 150 may also be configured as a loose external length of cable/cord that can optionally be held about a cord support/mount on the pole body 10*b* and/or on the body of the power unit 15.

Although the power unit 15 is shown with eight separate electrical receptacles 25, it may include less or more, e.g., a single receptacle or between 2-10 circumferentially spaced apart receptacles 25, in some embodiments.

In some embodiments, the power cord 150 can have a length that is a length of a hospital bed plus between 2-6 feet, typically between about 8-12 feet such as about 8 feet, about 8.5 feet, about 9 feet, about 9.5 feet, about 10 feet, about 10.5 feet, about 11 feet, about 11.5 feet and about 12 feet. The cord 150 can have a suitable power and amperage rating and associated diameter for supplying the power input 15*i* (FIG. 10A, 10B, 11) to the power circuit 15*c* of the onboard power unit 15. The cord 150 can have a 110 volt, 15 to 20 amperage rating. The cord 150 can comprise a 10 gage wire size.

Referring to FIG. 4A-4D, in some embodiments, the power unit 15 can orient the receptacles 25 in different directions or the unit 15 can have at least one that faces a different direction than another, e.g., one that faces the front, one that faces the back, one that faces a side or wing 10*w*, and the like. The power unit 15 can have one or more individually rotatable (swivel) electrical receptacles 25 as shown by the arrows adjacent two of the respective receptacles 25 for altering orientation. One or all of the receptacles 25 may have a fixed receptacle orientation.

Figure 4A:
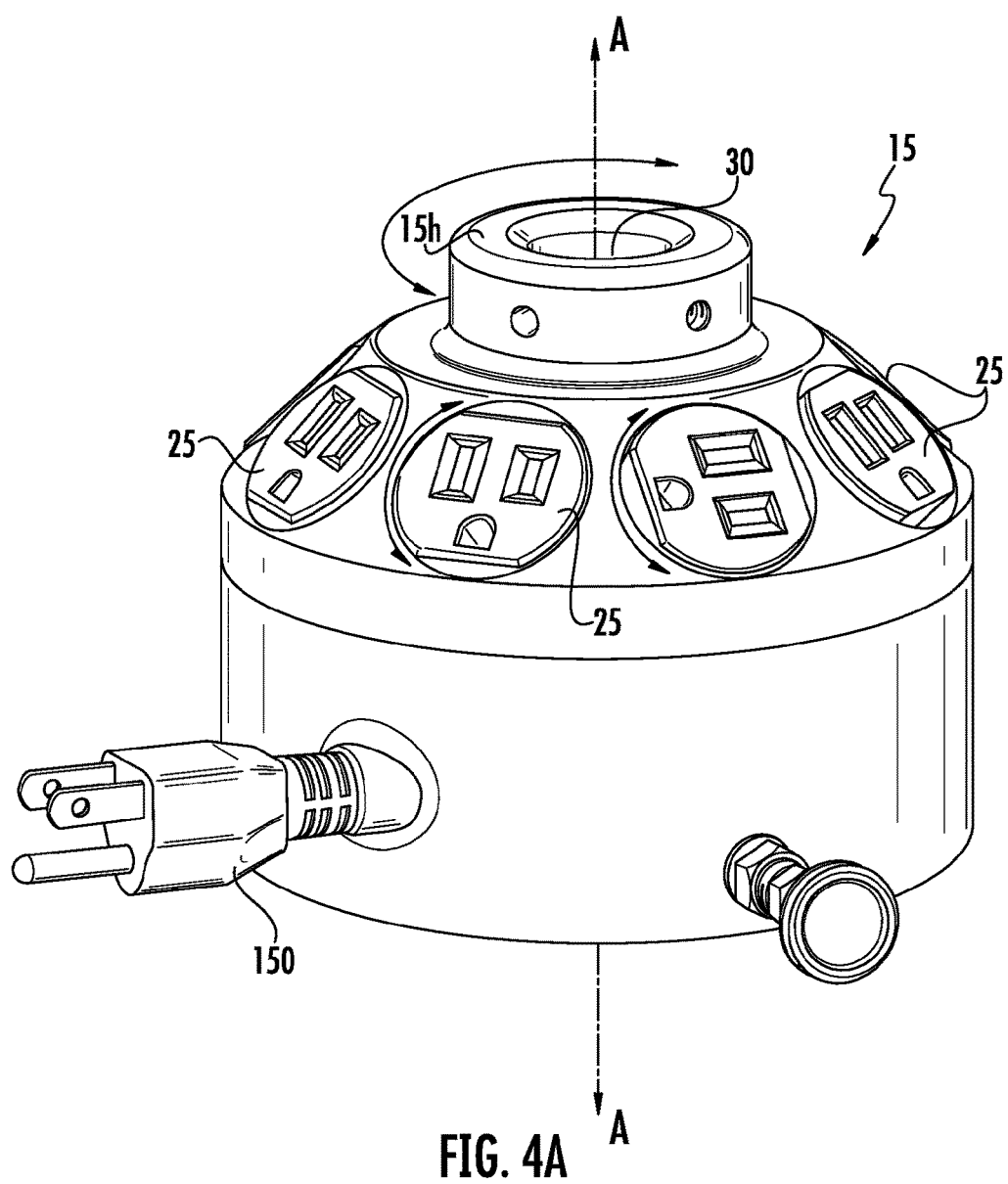
FIG. 4A is a greatly enlarged front perspective view of an exemplary power unit according to embodiments of the present invention.

Referring to FIG. 4A, the power unit 15 can have a housing 15*h* that rotates about the vertical axis A of the pole 10. The angular rotation of the housing 15*h* can be between 30-360 degrees, including about 30 degrees, about 60 degrees, about 90 degrees, about 120 degrees and about 180 degrees. The plug-in receptacle 25*r* rotation and/or rotation of the housing 15*h* can allow easier access of cords for various accessory components held by the pole 10 that may need powering, such as monitors, pumps and the like.

As shown in FIG. 4A-4D, the power unit housing 15*h* can have a longitudinally extending open center channel 30 that is sized and configured to surround the tubular pole body 10*b*. The channel 30 can have a diameter between about 1.25 inches and about 2 inches and a length between about 2 inches and about 4.5 inches.

Figure 4B:
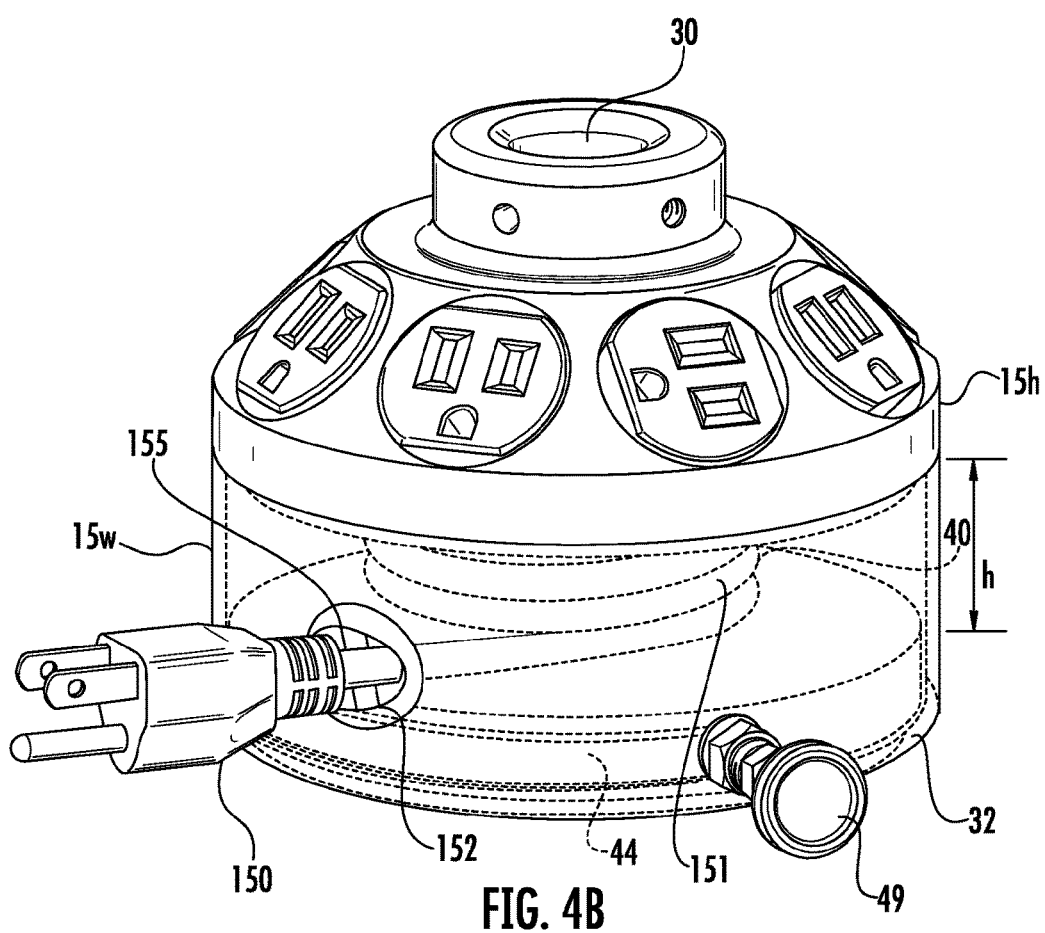
FIG. 4B is a partially transparent view of the device shown in FIG. 4A.
Figure 4C:
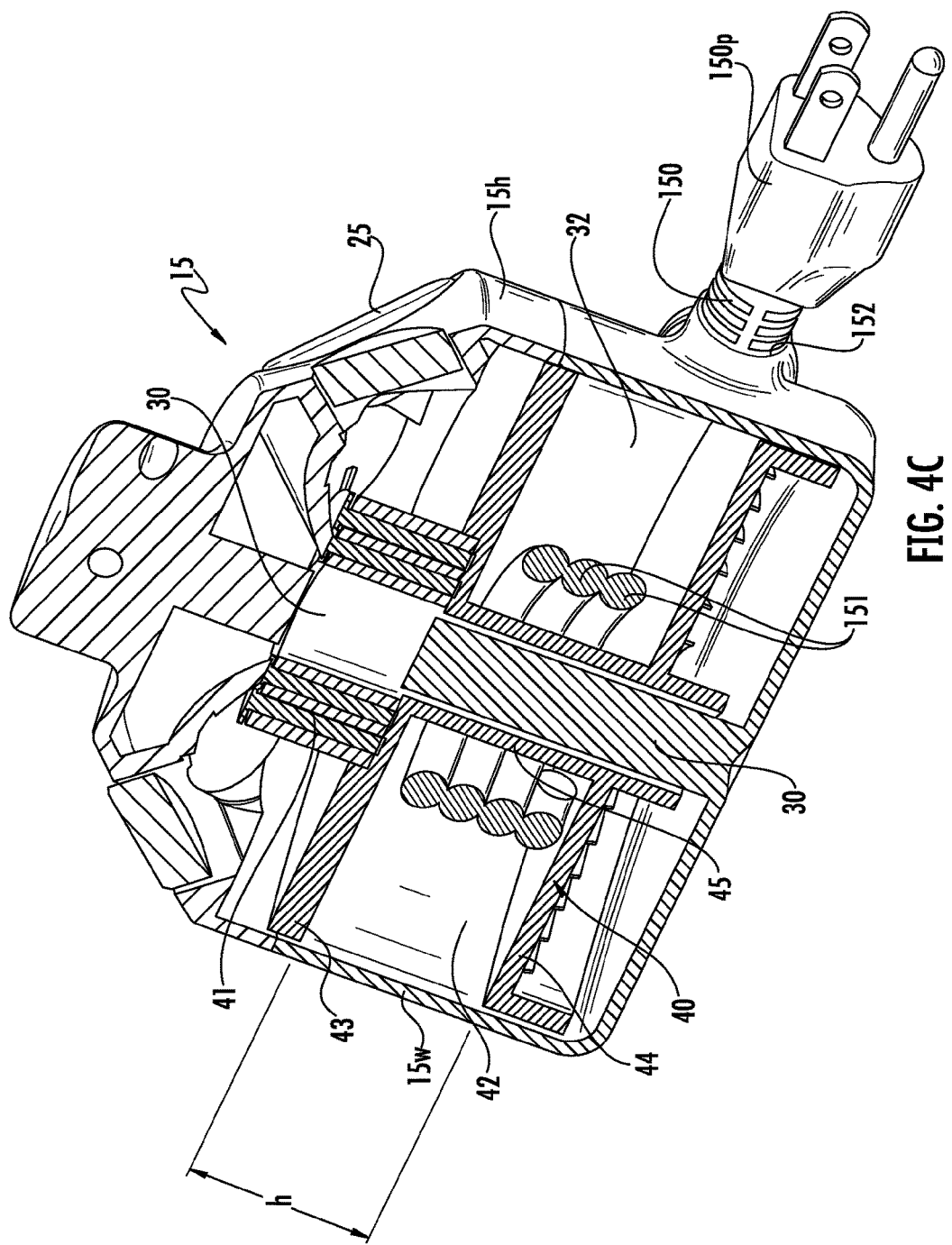
FIG. 4C is a sectional view of the device shown in FIG. 4A according to some embodiments of the present invention.
Figure 4D:
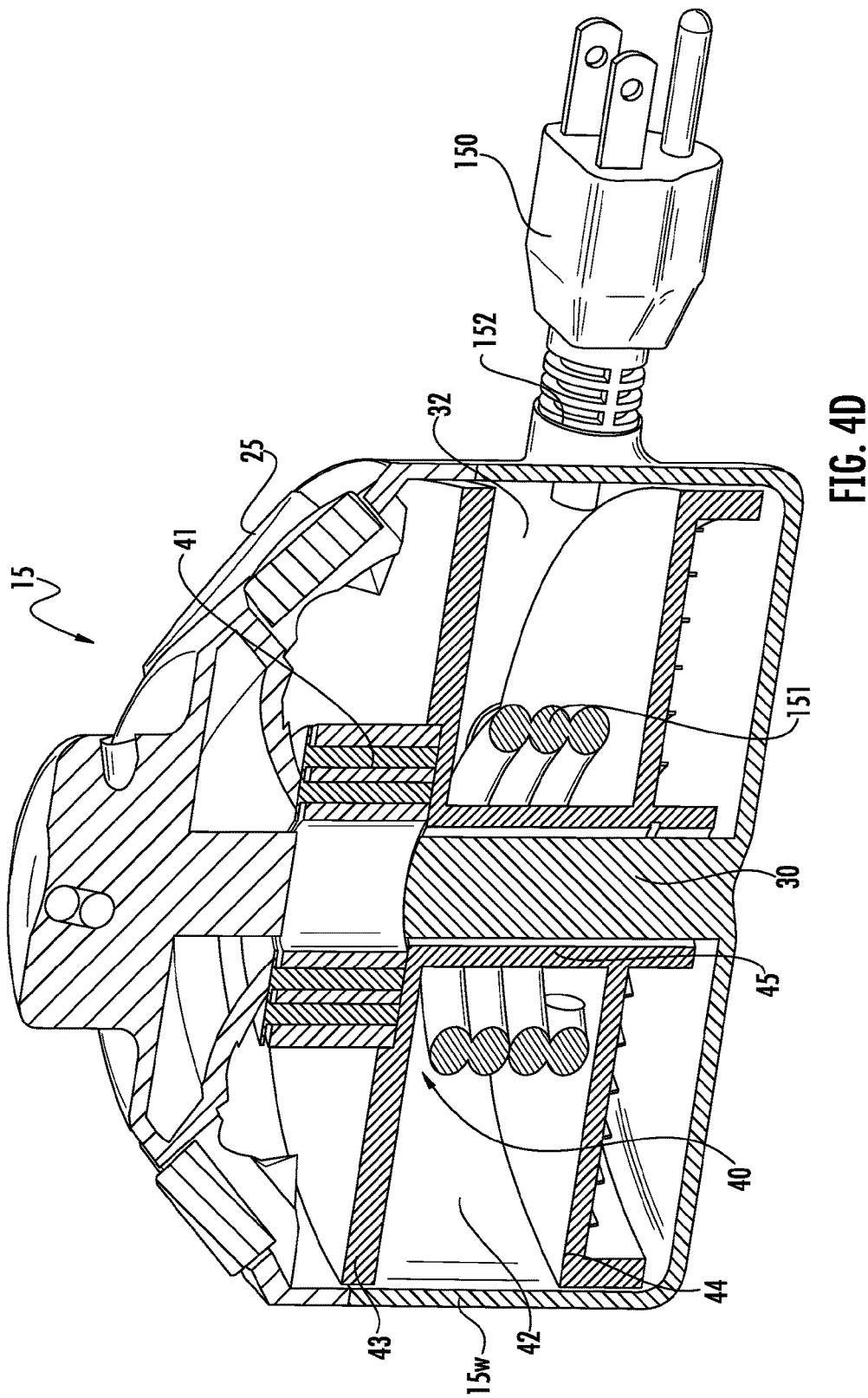
FIG. 4D is a partially transparent view of the sectional view shown in FIG. 4C.

FIG. 4B-4D show that the housing 15*h* can have a cord port 152 and an internal open vertical space extending below (as shown) or above the receptacles 25 with a vertical height "h" sufficient to accommodate a cord retraction mechanism 40 with a plurality of stacked layers/loops 151 of cord extending about and inside the channel 30 of the housing 15*h*.

The retraction mechanism 40 can be configured to be able to automatically or semi-automatically extend and/or retract the power cord 150, e.g., act as a rotatable "take-up" reel. To be clear, the term "retraction mechanism" refers to a mechanical or electromechanical device that can be used to either extend or retract or both extend and retract a length of power cord from an enclosure/unit housing 15*h*. The retraction mechanism 40 can have a rotation coupler 41 that can rotate the cord compartment 42 in the housing open space 32 that holds the stacked layers of cord 151. The compartment 42 can have upper and lower members 43, 44 with a circular outer perimeter attached at an inner edge portion thereof by a downwardly extending inner wall 45 with a cylindrical opening that aligns with the longitudinally extending channel 30 of the unit housing 15*h*.

The housing 15*h* outer wall 15*w* can define the outer enclosure of the compartment members 43, 44. The compartment 42 can have a radial length extending from the inner wall 45 outward to the outer perimeter thereof that is between about 3-10 inches. The retraction mechanism 40 can be configured to operate with sufficient drag or torque so that the cord 150 is not allowed to retract or extend at a speed that may cause a tipping issue of the pole 10. The retraction mechanism 40 can include a preloaded spring providing constant or substantially constant cord retention force (e.g., within about 10% of a defined cord retention force). The retraction mechanism 40 can include a spring loaded plunger 49 (FIG. 4B) that holds the spring and can provide a radially inwardly extending cord retention force onto the cord compartment through the power unit housing 15*h*, e.g., from either the upper compartment member 43 and/or lower compartment member 44 (FIG. 4C), typically via only the lower compartment member 44.

In some embodiments, the unit housing 15*h* can include a cord lock 155 (FIG. 4A) to electronically lock and/or allow a user to manually lock and/or unlock the cord 150 at a desired external length and/or to retain the cord 150 inside the housing 15*h* until pole 10 is in a stable environment or position. Although FIG. 4A illustrates a lock 155 adjacent the cord port 152, it may alternatively or additionally be inside the housing adjacent the retraction mechanism to inhibit rotation of the rotation coupler 41.

The pole 10 can have a user input 10*i* (FIG. 11) that allows a user to affirmatively indicate when an action to deploy the power cord or the retract the power cord is desired. The user input can be a manual and/or electrical input. The user input 10*i* can be in communication with the lock 155 and/or retraction mechanism 40 to allow a user to selectively extend and/or retract the power cord 150. In some embodiments, the lock 155 can lock the power cord 150 to prevent extension from the housing 15*h* until the housing 15*h* itself is locked into a desired circumferential orientation (such as where the unit housing 15*h* is able to rotate about the pole axis A).

Figure 5:
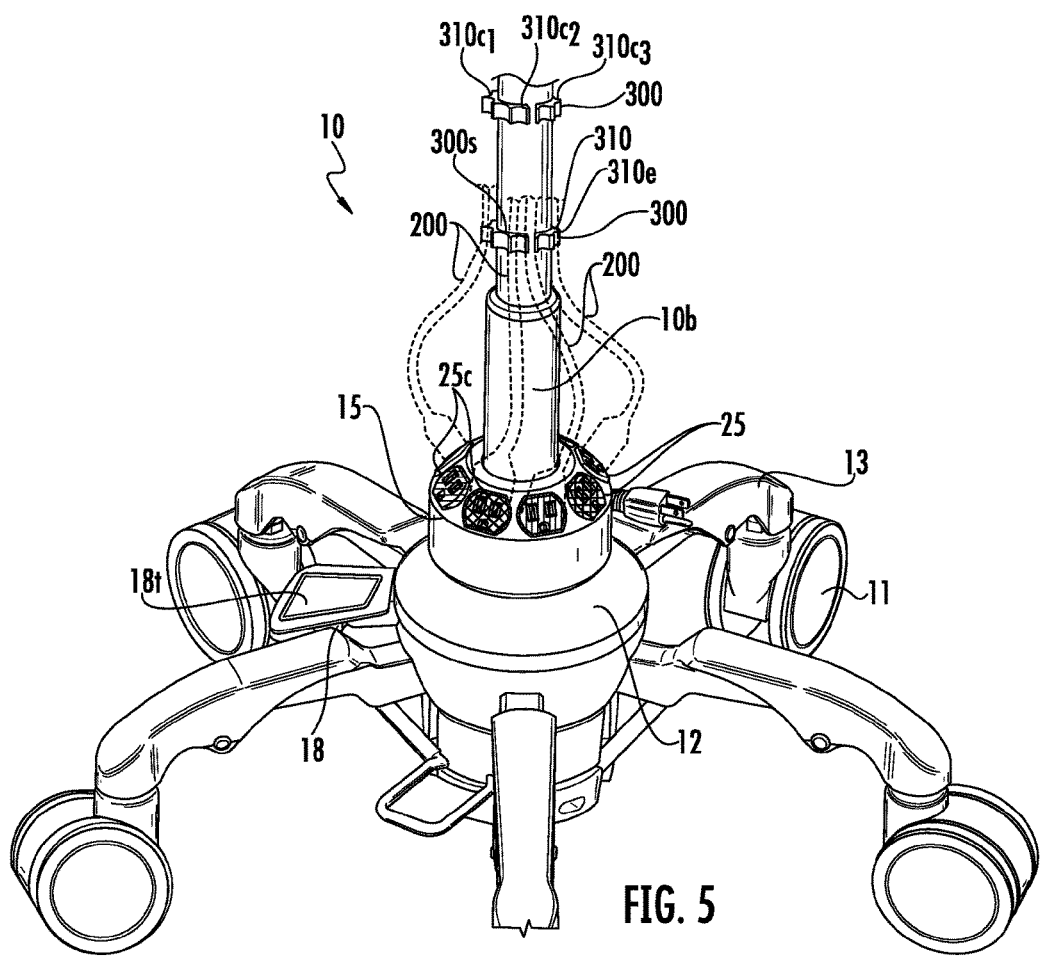
FIG. 5 is a side perspective view of another embodiment of a pole with an on-board power unit according to embodiments of the present invention.

FIG. 5 illustrates that the onboard power unit 15 of the pole 10 can have at least two receptacles 25 that have a different color 25*c* from each other (indicated by the different surface shadings/finishes on respective receptacles). In some embodiments, each receptacle 25 can have a different visual appearance such as one or more of a different color 25*c*, opacity, intensity or hue to allow a user to visually identify what receptacle 25 is used for a particular accessory power cord 200 to an accessory held by the pole 10. In some embodiments, as shown in FIG. 5, the pole 10 can also include at least one accessory cord grip 300 with circumferentially spaced apart longitudinally extending cord grip channels 310. The cord grip 300 can be integrated into the outer wall of the pole and/or can be provided as a removable sleeve 300*s* (as shown). For the integrated version, the pole 10 can comprise one or more overmolded segment with polymeric and/or elastomeric cord grips. The cord channels 310 can have an open externally facing perimeter segment 310*e*. The channels 310 can elastically deform to receive and snugly hold a respective accessory cord 200.

In some embodiments, the pole 10 can hold a plurality of the cord grips 300, one above another for limiting dangling cords for overhead accessories.

In some embodiments, the cord grips 300 can be configured with two or more channels 310 having a different color channel 310, such as $310c_1$, $310c_2$, $310c_3$. Optionally, the different color channels 310*c* can be color-coded to match a respective color 25*c* of a receptacle 25.

FIG. 6 illustrates that the power unit housing 15*h* can be configured to lockingly engage the pole 10 to lock into a desired circumferential orientation, when the unit housing 15h is rotatable about the pole axis A, such as using one or more cooperating lock and release members such as a radially extending finger 19 and radially extending slot 23. As shown in FIG. 6, the pole 10 can have at least one finger 19 and the unit housing can have a cooperating at least one slot 23. As also shown in FIG. 6, the unit housing (bottom) can have at least one finger 19 and the pole base 12 can have a cooperating at least one slot 23 configuration. While the radially extending slot 23 is shown on the base 12 and upper unit housing segment 15h and the radially extending finger 19 is shown on the lower unit housing 15h and the pole 10, these configurations can be reversed (and both are not required). Other radial-position lock configurations may be used.

FIG. 7 illustrates that the power unit 15 can have vertically stacked receptacles 25, at least one above at least one other. Both the upper and lower 15u, 15l receptacle compartments can rotate or both can be stationary or one can rotate and one can be stationary. Each of the receptacles in the upper and lower receptacle compartments 15u, 15l can be in electrical communication with a single power cord 150 or each can be in communication with a separate respective power cord 150.

The receptacles 25 can have front faces that angle outward from the pole 10 at an angle from horizontal at between 30-60 degrees, typically about 45 degrees.

Figure 8:
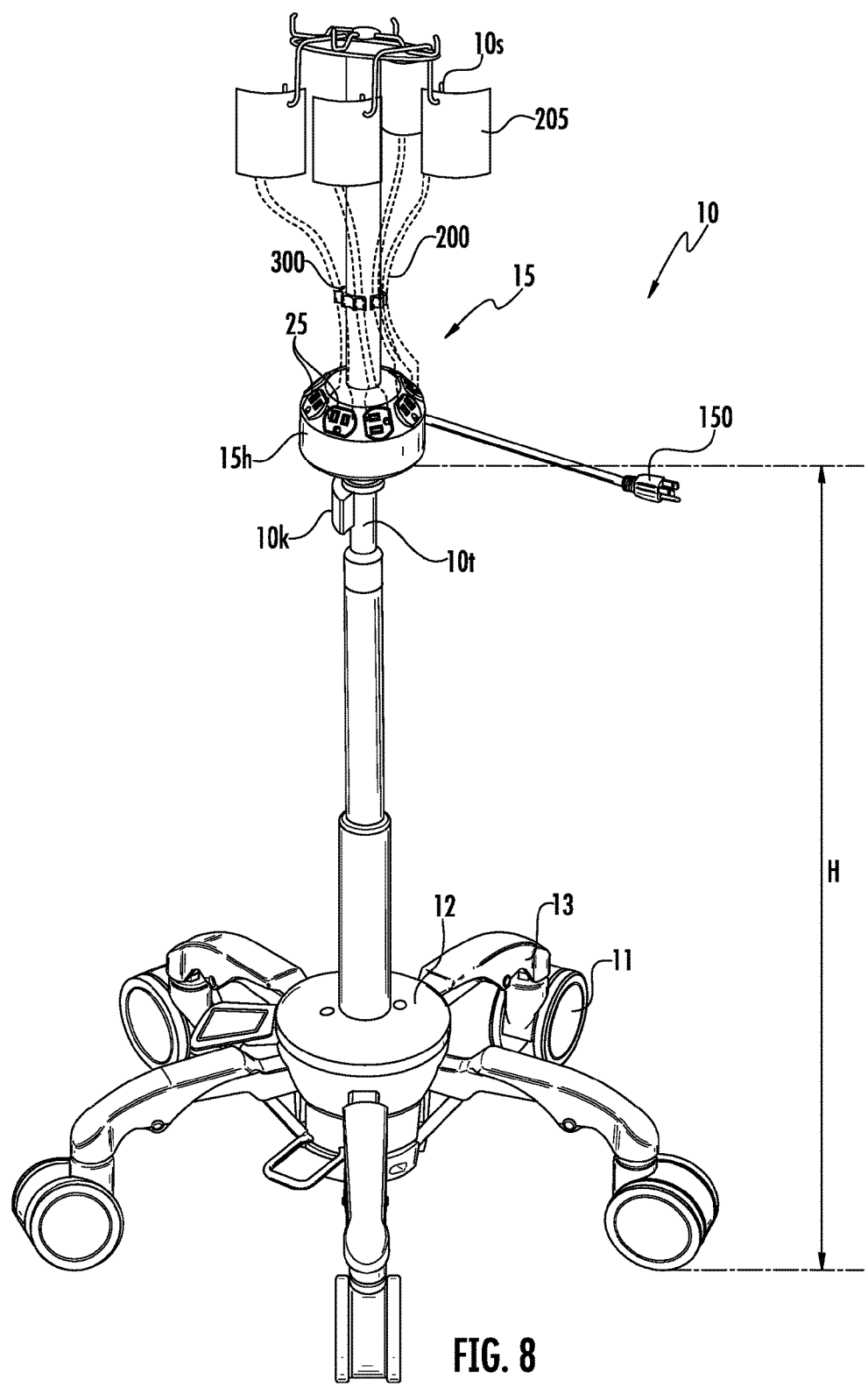
FIG. 8 is a side perspective view of another embodiment of a pole with an on-board power unit according to embodiments of the present invention.
Figure 9:
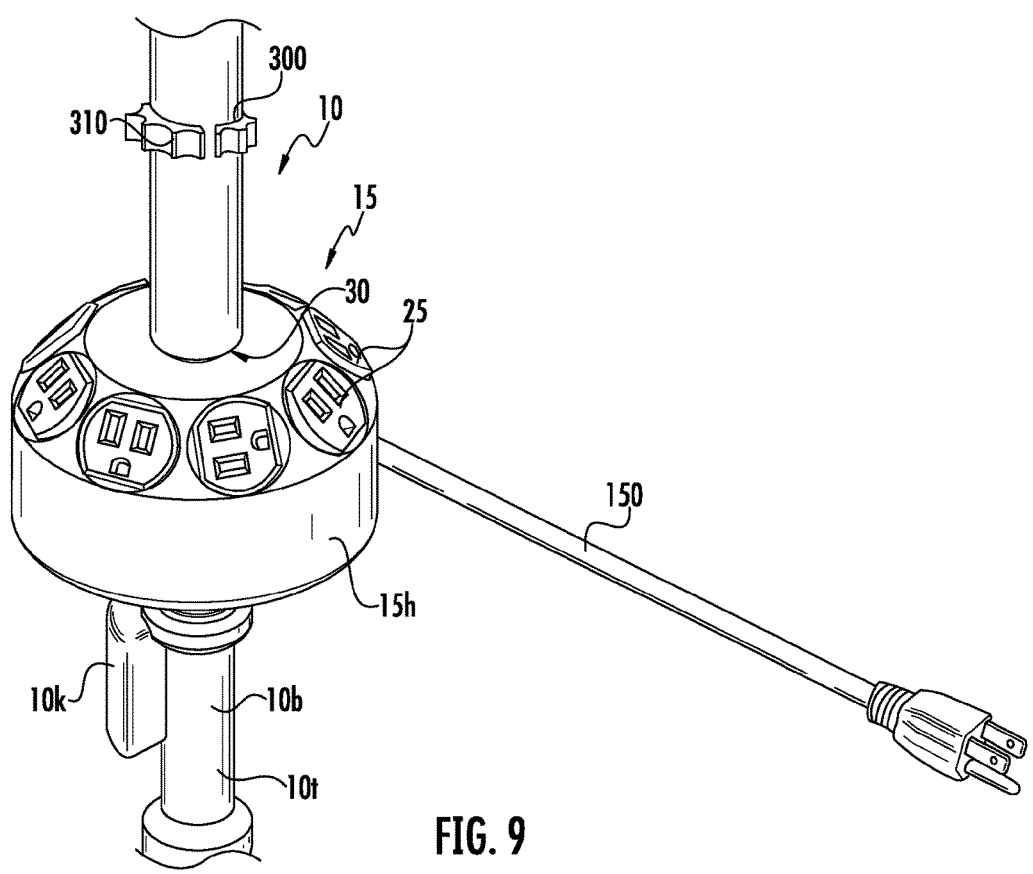
FIG. 9 is an enlarged view of the device shown in FIG. 8.

FIG. 8 and FIG. 9 illustrate another embodiment of the power unit 15. In this embodiment, the power unit 15 can reside in a fixed vertical position and may rotate circumferentially as described above. As shown, the power unit 15 can reside above a key 10k that cooperates with a docking interface of a boom arm, hospital bed, gurney, wheelchair or the like to allow the pole legs/wheels to be retracted while the pole 10 is suspending in the docking interface. The key 10k can have an arcuate longitudinally extending shape, as shown, the key 10k may have a circumferential angular extent of between about 15 and 45 degrees, for example. The key 10k can reside on the pole body 10b at a tubular segment 10t with a smaller outer diameter relative to at least an underlying segment of the pole.

The power unit 15 can be held at position closer to the accessory devices 205 with associated power cords 200 which may lessen power cord lengths, and may avoid undue lengths of accessory cords 200 which may otherwise be located adjacent a floor. The accessory devices 205 are powered accessory devices such as pumps, monitor and the like. The power unit 15 can be positioned at a height H above the floor when the wheels 11 are on the floor, that is between about 3-5 feet, such as at about 3 feet, at about 3.5 feet, at about 4 feet or about 4.5 feet.

In this embodiment, as shown in FIG. 9, a cord grip 300 with cord channels 310 may be used.

Figure 10A:
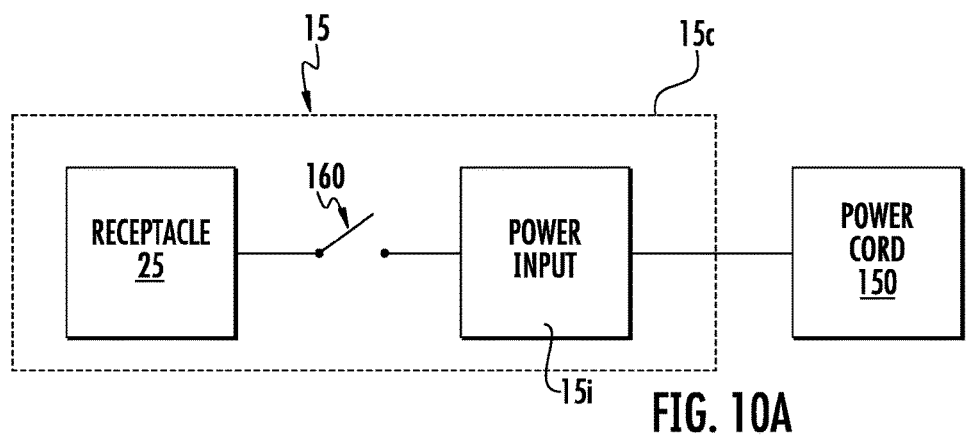
FIGS. 10A, 10B and 11 are schematic illustrations of a power circuit for an on-board power unit of an accessory pole according to embodiments of the present invention.
Figure 10B:
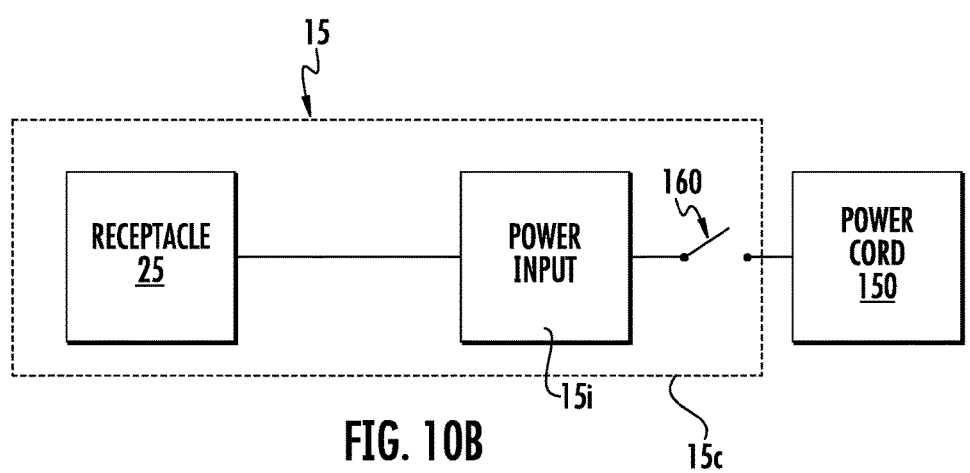
Figure 11:
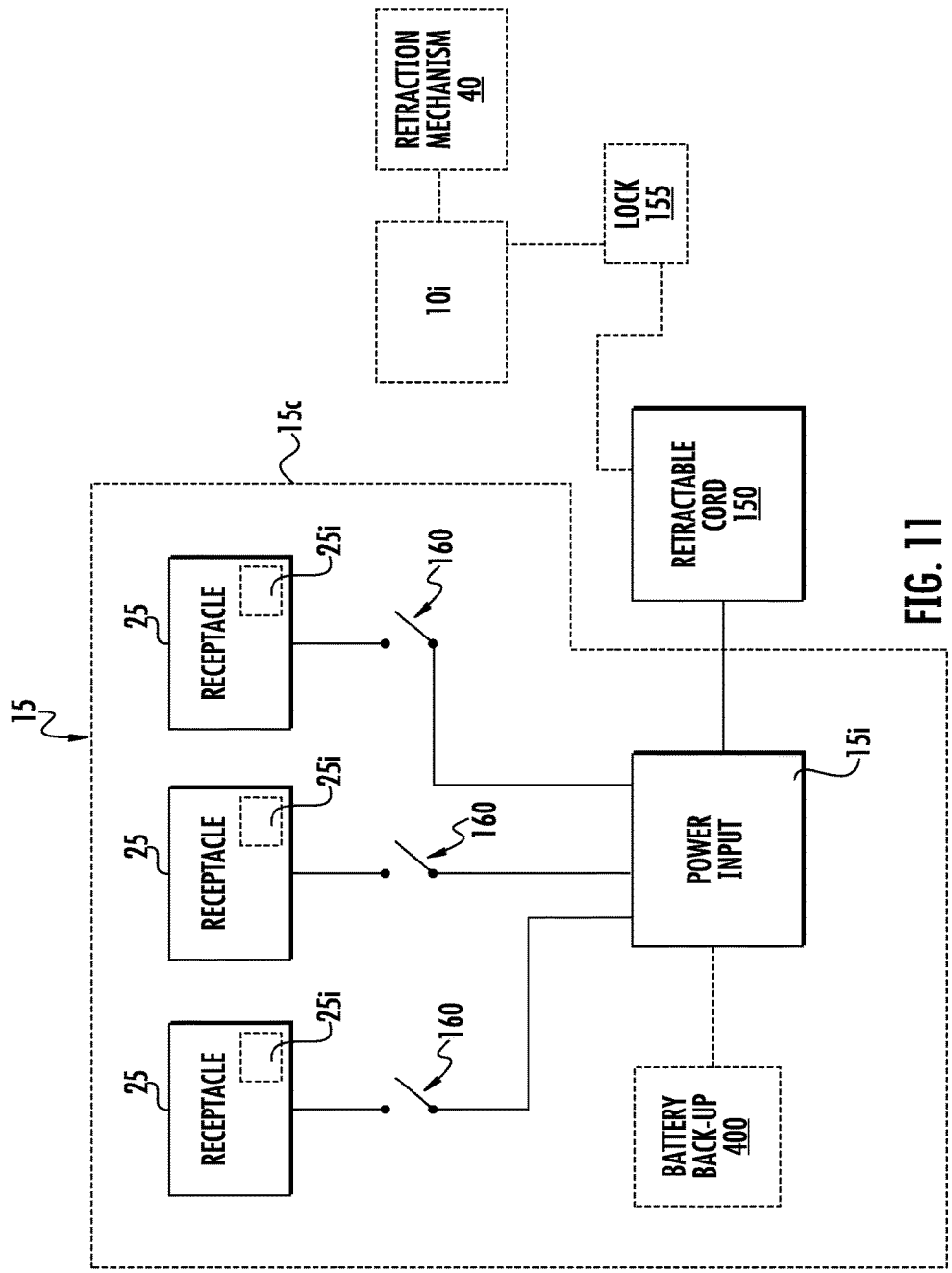

FIGS. 10A, 10B and 11 illustrate examples of a power circuit 15c for a power unit 15. FIGS. 10A and 10B show that the power circuit 15c includes a power input 15i from the power cord 150. The power circuit 15c can include at least one surge protector 160.

FIG. 11 also shows that the onboard unit 15 can include at least one battery 400 that can be used to power at least one of the receptacles 25 in the case of an emergency, black-out or ambulatory movement of the pole 10. The receptacle 25 with the onboard battery power source 400 can have a different external visual indicia (color, configuration, text, shape) to provide a distinct visual look or configuration so that a user can plug in a critical component into the receptacle 25 with the battery power.

FIG. 11 also shows that the receptacles can have one or more indicator lights 25i to indicate when it is powered or not or when a fault condition is identified, for example.

The poles with onboard power units 15 can be configured for various purposes and/or provided as components of various devices. The poles can be configured to be one or more of an IV pole, an oxygen tank pole, a monitor support pole, a pole attachable to a pediatric wagon, wheelchair or hospital bed or hospital beds with a pole docking system and/or any combination of the different uses and may be used for other hospital or care-based medical accessories.

The above disclosure is intended to be illustrative and not exhaustive. This description will suggest many variations and alternatives to one of ordinary skill in this art. Thus, the foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention. Therefore, it is to be understood that the foregoing is illustrative of the present invention and is not to be construed as limited to the specific embodiments disclosed, and that modifications to the disclosed embodiments, as well as other embodiments, are intended to be included within the scope of the invention.

Further, the particular features presented in the dependent claims can be combined with each other in other manners within the scope of the invention such that the invention should be recognized as also specifically directed to other embodiments having any other possible combination of the features of the dependent claims. For instance, for purposes of claim support, any dependent claim which follows from an independent claim should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims).

That which is claimed:

1. A medical accessory support pole, comprising:
an elongate pole body defining a longitudinal pole axis;
a plurality of wheels attached to the pole body; and
an onboard power unit held by the pole body, comprising:
    a housing having a downwardly extending cylindrical channel surrounding a segment of the pole body, the housing further including a neck that angles out to a receptacle surface and then merges into a vertical segment that extends up and/or down a vertical distance to define a cord compartment;
    a plurality of circumferentially spaced apart electrical receptacles; and
    a power cord in electrical communication with the electrical receptacles extending outward from the housing;
    wherein the cord compartment is rotatable inside the housing about the longitudinal pole axis.

2. The pole of claim 1, further comprising a power cord retraction mechanism held by the housing in communication with the power cord to allow automatic or semi-automatic retraction of the power cord into the housing.

3. The pole of claim 1, wherein the power cord has a length of between 5-12 feet, and, in a fully or partially retracted configuration, a length of the power cord resides inside the housing in stacked circular layers about the cylindrical channel.

4. The pole of claim 2, wherein the retraction mechanism comprises a rotation coupler in communication with a compartment holding a length of the power cord.

5. The pole of claim 1, wherein the pole is a transformable pole having a plurality outwardly extending legs holding a respective wheel, wherein the transformable pole has a first extended configuration with the legs extending outward away from the pole body with the wheels on a floor and a second configuration where the legs are retracted to reside closer to the pole body and the wheels are lifted off the floor, and wherein the onboard power unit is configured to longitudinally slide up and down in concert with a base as the legs retract and extend, respectively.

6. The pole of claim 1, further comprising at least one cord grip attached to the pole body, the cord grip comprising a plurality of circumferentially spaced apart and longitudinally extending accessory cord channels for holding segments of longitudinally extending accessory power cords.

7. The pole of claim 1, wherein at least one of the electrical receptacles has an externally visual color that is different from one or more other of the electrical receptacles.

8. The pole of claim 1, wherein the power unit housing is rotatable about a vertical pole axis of the pole body.

9. The pole of claim 1, wherein one or more of the electrical receptacles has a different socket orientation from another of the electrical receptacles.

10. The pole of claim 1, wherein one or more of the electrical receptacles can be rotated to provide a desired socket orientation.

11. The pole of claim 1, wherein the housing has an angled outer surface that extends away from the cylindrical channel and merges into a vertical outer wall, and wherein the angled outer surface is angled at between 30-60 degrees from horizontal.

12. The pole of claim 1, wherein the pole comprises wings held by an upper portion of the pole body and a base held adjacent the wheels, and wherein the housing resides a distance above the wheels by between 3-6 feet to reside closer to the wings of the pole than the base.

13. The pole of claim 1, wherein the pole body comprises a docking alignment key member circumferentially extending between 15-45 degrees and longitudinally extending between 1-5 inches of a segment of the pole body, wherein the segment of the pole body with the key member has a diameter that is less than a diameter of at least an adjacent lower portion of the pole body, wherein the housing resides a distance above the wheels by between 3-6 feet to reside above the key member, and wherein the housing comprises an outer wall that extends radially outward a greater distance from the pole body than the key member.

14. A medical accessory support pole, comprising:
an elongate pole body defining a longitudinal pole axis;
a base attached to a lower portion of the pole body comprising a plurality outwardly extending legs;
a plurality of wheels attached to the legs, wherein the legs have a first extended configuration with the legs extending outward away from the pole body with the wheels on a floor and a second configuration where the legs are retracted to reside closer to the pole body and the wheels are lifted off the floor; and
an onboard power unit attached to the pole body, comprising:
a housing having a downwardly extending cylindrical channel surrounding a segment of the pole;
a plurality of electrical receptacles spaced apart around a circumference of the longitudinal pole axis;
a power cord in electrical communication with the electrical receptacles extending outward from the housing; and
a power cord retraction mechanism held by the housing in communication with the power cord to allow automatic or semi-automatic retraction of the power cord into the housing, wherein the power cord has a length of between about 5 feet and about 12 feet, and, in a fully or partially retracted configuration, a length of the power cord resides inside the housing in stacked circular layers about the cylindrical channel,
wherein the onboard power unit is configured to longitudinally slide up and down in concert with the base as the legs retract and extend, respectively.

15. The pole of claim 14, wherein the housing is rotatable about the pole body, and wherein the housing comprises a power cord compartment that is configured to rotate inside the housing about the pole.

16. A medical accessory support pole, comprising:
an elongate pole body defining a longitudinal pole axis;
a base attached to a lower portion of the pole body comprising a plurality outwardly extending legs;
a plurality of wheels attached to the legs, and wherein the legs have a first extended configuration with the legs extending outward away from the pole body with the wheels on a floor and a second configuration where the legs are retracted to reside closer to the pole body and the wheels are lifted off the floor; and
an onboard power unit attached to the pole body, comprising:
a housing having a downwardly extending cylindrical channel surrounding a segment of the pole;
a plurality of electrical receptacles spaced apart around a circumference of the longitudinal pole axis;
a power cord in electrical communication with the electrical receptacles extending outward from the housing; and
a power cord retraction mechanism held by the housing in communication with the power cord to allow automatic or semi-automatic retraction of the power cord into the housing,
wherein the power cord has a length of between about 5 feet and about 12 feet, and, in a fully or partially retracted configuration, a length of the power cord resides inside the housing in stacked circular layers about the cylindrical channel,
wherein the pole comprises wings held by an upper portion of the pole body, and wherein the housing resides a distance above the wheels by between 3-6 feet to reside closer to the wings of the pole than the base.

17. The pole of claim 16, wherein the pole body comprises a docking alignment key member circumferentially extending between 15-45 degrees and longitudinally extending between 1-5 inches about a segment of the pole body, wherein the segment of the pole body with the key member has a diameter that is less than a diameter of at least an adjacent lower portion of the pole body, wherein housing resides above the key member, and wherein the housing comprises an outer wall that extends radially outward a greater distance from the pole body than the key member.

18. The pole of claim 16, wherein the housing is rotatable about the pole body, and wherein the housing comprises a power cord compartment that is configured to rotate inside the housing about the pole.

19. A method of providing power to hospital equipment, comprising:

provide a substantially vertical hospital support pole with a plurality of rollers and/or casters and comprising an on-board power shroud with a plurality of electrical receptacles;

rolling the hospital support pole across a floor;

extending a power cord held in stacked circular layers inside a cord compartment of the on-board power shroud to have an exposed length, the stacked circular layers surrounding a segment of the hospital support pole; and plugging in the power cord to an electrical receptacle of a hospital electrical circuit to power the receptacles of the on-board power shroud, then optionally, in response to a user unplugging the power cord, automatically retracting the exposed length of the power cord back into the cord compartment, and/or optionally electro-mechanically or mechanically automatically raising the hospital support pole so that the rollers and/or casters are off floor before, during or after plugging in the power cord.

\* \* \* \* \*